(12) United States Patent
Celebi

(10) Patent No.: US 6,402,790 B1
(45) Date of Patent: Jun. 11, 2002

(54) ANGULARLY ADJUSTABLE REVERSIBLE PROSTHETIC DEVICE

(76) Inventor: Dogan Celebi, 4858 Battery La., Apt. #201, Bethesda, MD (US) 20814

( * ) Notice: Subject to any disclaimer, the term of this patent is extended or adjusted under 35 U.S.C. 154(b) by 0 days.

(21) Appl. No.: 09/621,297

(22) Filed: Jul. 20, 2000

(51) Int. Cl.[7] .............................. A61F 2/80; A61F 2/64; A61F 2/66
(52) U.S. Cl. .............................. 623/38; 623/47; 623/53
(58) Field of Search ............................ 623/38, 47, 48, 623/53, 44, 45

(56) References Cited

U.S. PATENT DOCUMENTS

| | | | |
|---|---|---|---|
| 5,405,410 A | | 4/1995 | Arbogast et al. ............. 623/47 |
| 5,464,441 A | * | 11/1995 | Phillips ....................... 623/27 |
| 5,549,711 A | * | 8/1996 | Bryant ........................ 623/53 |
| 5,800,564 A | * | 9/1998 | Gelineau ..................... 623/38 |
| 5,800,565 A | | 9/1998 | Biedermann ................. 623/38 |
| 5,888,232 A | | 3/1999 | Taylor ......................... 623/38 |
| 5,997,583 A | * | 12/1999 | Woolnough et al. ......... 623/38 |

* cited by examiner

Primary Examiner—Corrine McDermott
Assistant Examiner—Alvin Stewart
(74) Attorney, Agent, or Firm—Henderson & Sturm LLP

(57) ABSTRACT

An angularly adjustable reversible prosthetic leg device (10) for use with a prosthetic socket (100) having a tube clamp adapter (101). The prosthetic leg device (10) includes an integrally formed leg pylon member (20) having an upper segment (22) adapted to be engaged by the tube clamp adapter (101), a concavo-convex intermediate segment (23), and a generally cylindrical lower segment (24) that is adapted to be reversibly received and angularly adjustable relative to the ankle segment (41) of a foot member (40) which also includes a toe segment (42) and a heel segment (43).

20 Claims, 4 Drawing Sheets

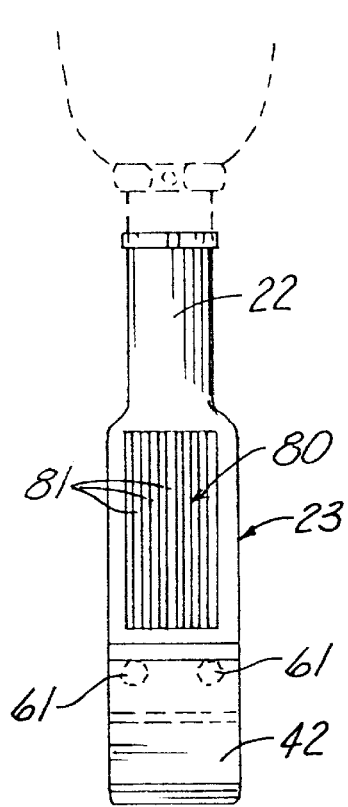
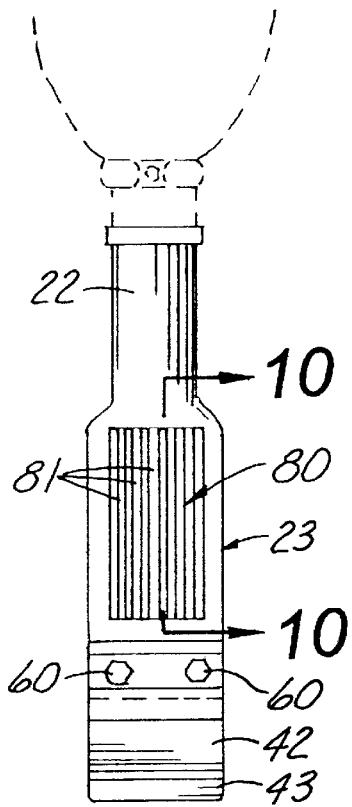
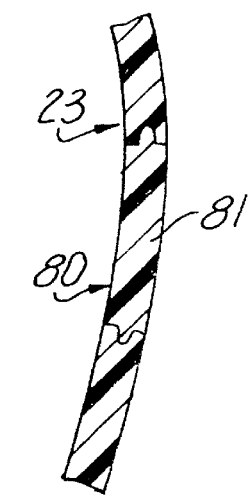
Fig. 8  Fig. 9  Fig. 10
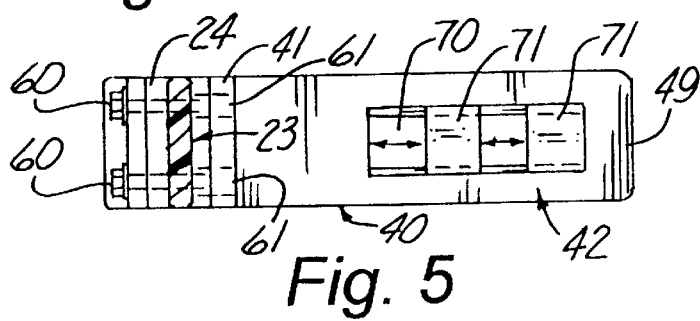
Fig. 5
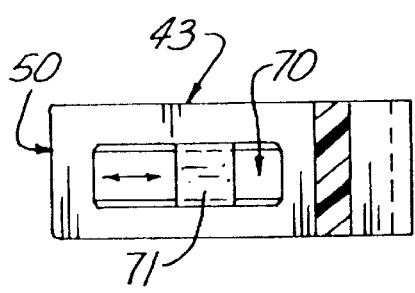
Fig. 6
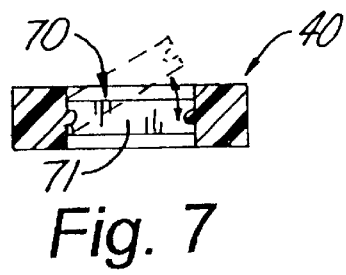
Fig. 7

ANGULARLY ADJUSTABLE REVERSIBLE PROSTHETIC DEVICE

BACKGROUND OF THE INVENTION

1. Field of the Invention

The present invention relates to the field of prosthetic devices in general, and in particular to a reversible variable angle prosthetic leg device whose flexibility/rigidity can be selectively varied.

2. Description of Related Art

As can be seen by reference to the following U.S. Pat. Nos. 5,405,410; 5,800,565; 5,888,232; and 5,997,583, the prior art is replete with myriad and diverse prosthetic leg devices. In addition, U.S. Pat. No. 5,464,441 discloses a prosthetic leg device that employs a concavo-convex portion to enhance the flexibility of the prosthetic device.

While all of the aforementioned prior art constructions are more than adequate for the basic purpose and function for which they have been specifically designed, they are uniformly deficient with respect to their failure to provide a simple, efficient, and practical arrangement wherein both the leg and foot portions of the prosthetic leg device are angularly adjustable relative to one another and wherein the rigidity/flexibility of the prosthetic device can be varied in a number of ways.

As most users of prosthetic leg devices are all too well aware, virtually all of the commercially available prosthetic leg devices offer very little in the way of variable rigidity/flexibility for different mobile situations, nor do they feature any angular adjustment between the leg and foot portions of the device to accommodate footwear having different heel heights ranging from flats to short heels for men, as well as flats to high heels for women.

As a consequence of the foregoing situation, there has existed a longstanding need for a new and improved angularly adjustable variable resistance prosthetic leg device which will allow the user to quickly and simply make adjustments to the prosthetic leg device to accommodate the particular needs of the prosthetic wearer at any given time, and the provision of such a device is the stated objective of the present invention.

BRIEF SUMMARY OF THE INVENTION

Briefly stated, the prosthetic leg device that forms the basis of the present invention comprises in general, a leg unit, a foot unit, and an adjustment unit that can be used to vary the angular orientation of the leg unit relative to the foot unit. The invention also includes a number of methods of varying the rigidity/flexibility of both the overall device, as well as specific segments of the leg and foot units.

This invention essentially begins where the concavo-convex arrangement of the Phillips '441 patent left off in that there is a unique cooperation between the leg and foot units of this invention that permits the leg unit to be quickly and easily reversed 180° relative to the foot unit to convert the prosthetic leg device of this invention from a "walking" prosthetic to a "running" prosthetic.

In addition, the invention allows the leg unit to be angularly adjustable relative to the foot unit, and for both the leg unit and the foot unit to have means for adjusting the rigidity/flexibility of selected portions of each unit.

As will be explained in greater detail further on in the specification, the leg unit includes a leg pylon member having integrally formed upper, intermediate, and lower segments. The upper and lower segments have perpendicularly oriented generally cylindrical configurations and the intermediate segment has a generally thin flat concavo-convex configuration whose reversal relative to the foot unit produces dramatically different results from a rigidity/flexibility standpoint.

Furthermore, the foot unit includes an integrally formed foot member having an ankle segment, a toe segment, and a heel segment. The ankle segment is provided with an elongated arcuate recess that is dimensioned to laterally receive the generally cylindrical lower segment of the leg pylon member such that the concavo-convex intermediate segment of the leg pylon member can be disposed in oppositely facing directions relative to the foot member to produce a generally rigid "walking" configuration or a relative flexible "running" configuration.

As will also be explained in greater detail further on in the specification, the adjustment unit is designed to captively engage the lower segment of the foot pylon member in the arcuate recess of the ankle segment of the foot member at various angular orientations to accommodate footwear having different heel heights. Both the leg unit member and the foot unit have removable elements whose presence or absence will vary the relative rigidity/flexibility of selected portions of those units.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 5 is a cross sectional view of the device taken through line 5—5 of FIG. 2;

FIG. 6 is a cross sectional view of the device taken through line 6—6 of FIG. 2;

FIG. 7 is a cross sectional view of the device taken through line 7—7 of FIG. 2;

FIG. 8 is a front elevation view of the device;

FIG. 9 is a rear elevation view of the device;

FIG. 10 is a cross sectional view taken through line 10—10 of FIG. 9.

DETAILED DESCRIPTION OF THE INVENTION

Figure 1:
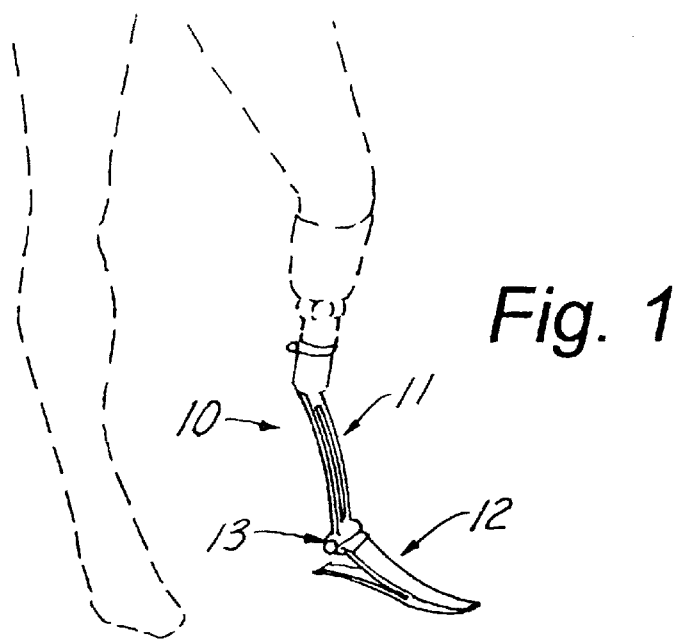
FIG. 1 is a perspective view of the angularly reversible adjustable prosthetic device oriented to provide more rigid support to the user's leg.

As can be seen by reference to the drawings, and in particular to FIG. 1, the angularly adjustable reversible prosthetic device that forms the basis of the present invention is designated generally by the reference number 10. The device 10 comprises in general, a leg unit 11, a foot unit 12, and an adjustment unit 13 which permits the leg unit 11 to be reversed and angularly adjusted relative to the foot unit 12. These units will now be described in seriatim fashion.

As shown in FIGS. 1 through 4, and 11, the leg unit 11 comprises a leg pylon member 20 which is integrally fabricated from a high density plastic material and includes a generally solid cylindrical upper segment 22, a generally thin concavo-convex shaped intermediate segment 23 and a generally hollow cylindrical lower segment 24. The upper segment 22 is dimensioned to be captively engaged within the tube clamp adapter 101 of a prosthetic socket 100.

In addition, the longitudinal axis of the generally cylindrical upper segment 22 has a vertical orientation, the curved intermediate segment 23 has a generally elongated rectangular cross sectional configuration, and the longitudinal axis of the generally hollow cylindrical lower segment 24 has a horizontal orientation.

Figure 11:
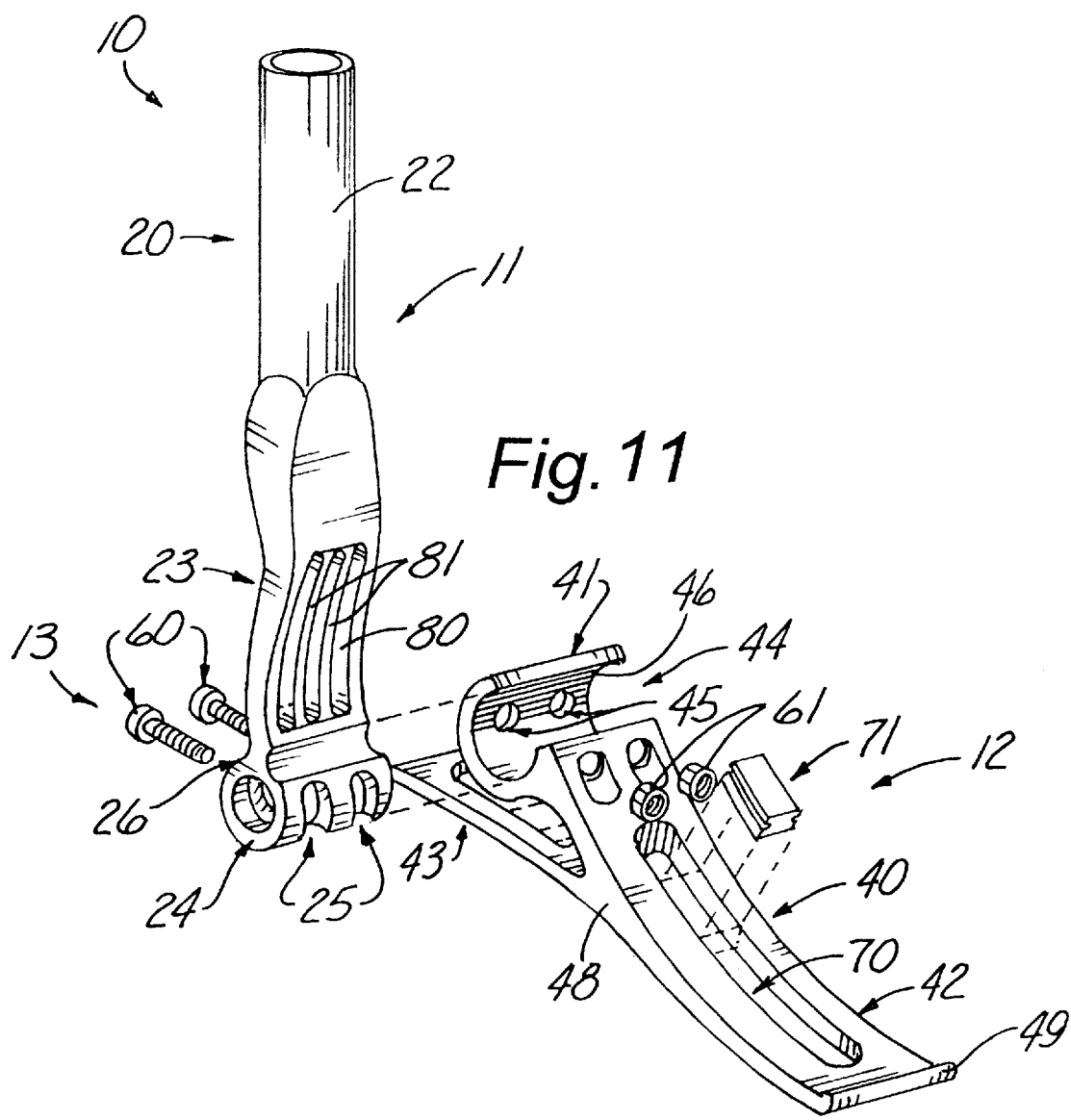
FIG. 11 is an exploded perspective view of the device.

As can best be seen by reference to FIG. 11, the generally hollow cylindrical lower segment 24 of the upper pylon member 20 is provided with a pair of elongated slots 25 that are oriented transverse to the longitudinal axis of the lower segment 24 and at least a portion of the external periphery of the lower segment 24 is provided with elongated ridged teeth 26 which are disposed parallel to one another and radially aligned relative to the longitudinal axis of the lower segment 24.

Still referring to FIG. 11, it can be seen that the foot unit 12 comprises a foot member 40 having an ankle segment 41, a toe segment 42, and a heel segment 43 formed integrally with one another from the same high density plastic material that is employed in the fabrication of the upper pylon member 20.

The ankle segment 41 includes an elongated arcuate ankle socket recess 44 that is dimensioned to slidably engage the hollow cylindrical lower segment 24 of the pylon member 20 when the lower segment 24 is inserted into the ankle socket recess 44 in a lateral fashion. The cylindrical lower segment 24 is pivotably secured within the ankle socket recess 44.

In addition, the ankle segment is further provided with a pair of apertures 45 that are dimensioned to receive the adjustment unit 13 and at least a portion of the interior surface of the arcuate ankle socket recess 44 is provided with elongated ridged teeth 46 that are disposed parallel to one another, radially aligned relative to the longitudinal axis of the arcuate recess 44 and adapted to releasably engage the ridged teeth 26 on the lower segment 23 of the pylon member 20.

Figure 4:
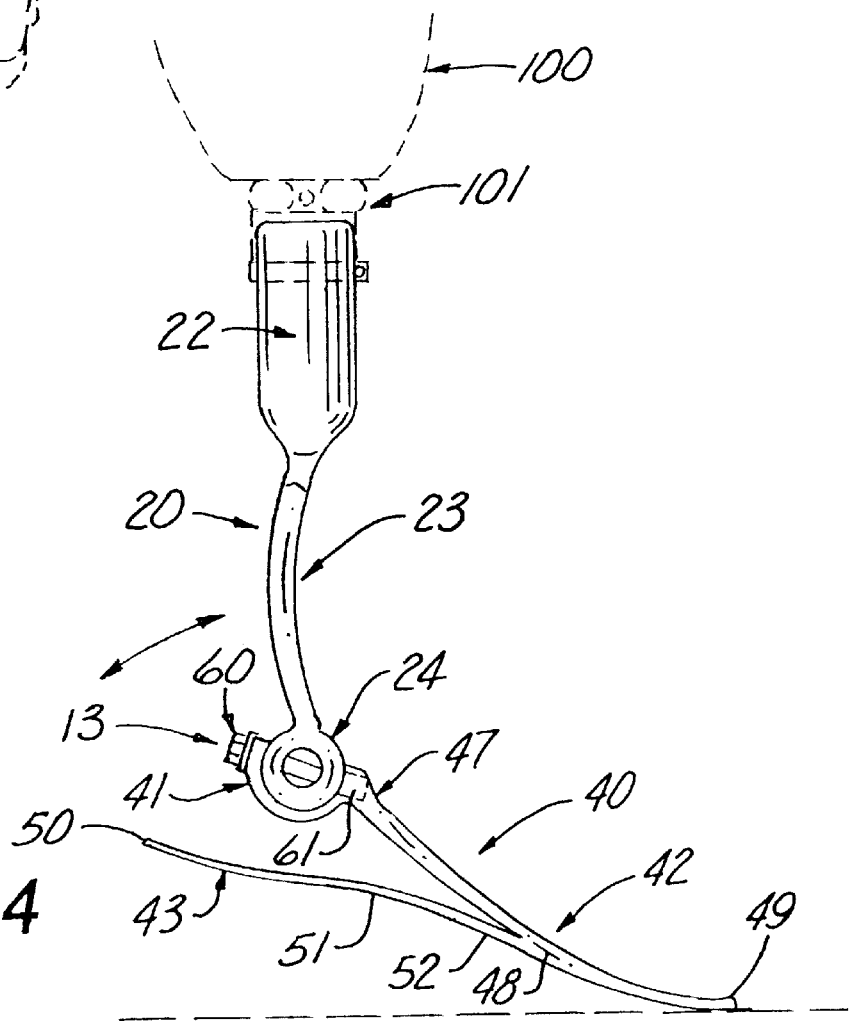
FIG. 4 is a side elevation view of the device in the more flexible support orientation.

As shown in FIG. 4, the toe segment 42 of the foot member 40 includes an inboard end 47 which originates as an elongated downwardly curved element extending outwardly from one side of the ankle segment 41 and having a downwardly curved thickened intermediate portion 48 and a generally tapered upwardly curved outboard end 49. In addition, the heel segment 43 has a generally tapered downwardly curved outboard end 50 and an intermediate transition section 51 which gradually thickens and transforms into an upwardly curved inboard end 52 which merges with the thickened intermediate portion 48 of the toe segment 42 in a generally Y-shaped configuration. The outboard end 50 of the heel segment 43 extends rearwardly of the ankle segment 41 of the foot member 40.

As can best be appreciated by reference to FIGS. 2, 4, 9, and 11, the adjustment unit 13 comprises a pair of threaded bolts 60 which are dimensioned to extend through the pair of apertures 45 in the ankle segment 41 of the foot member 40 and the pair of elongated slots 25 in the lower segment 24 of the foot pylon member 20. The inboard end of the threaded bolts 60 are adapted to be engaged in a pair of threaded metal sleeves 61 fixedly secured within the apertures 45 in the ankle segment 41 of the foot member 40.

As was mentioned previously in the specification, this invention does not claim to be the first prosthetic device that employs a concavo-convex leg pylon; however, it is believed to be the first time that a concavo-convex leg pylon has been employed in both a reversible and angularly adjustable fashion relative to the foot portion of the prosthetic device.

Figure 2:
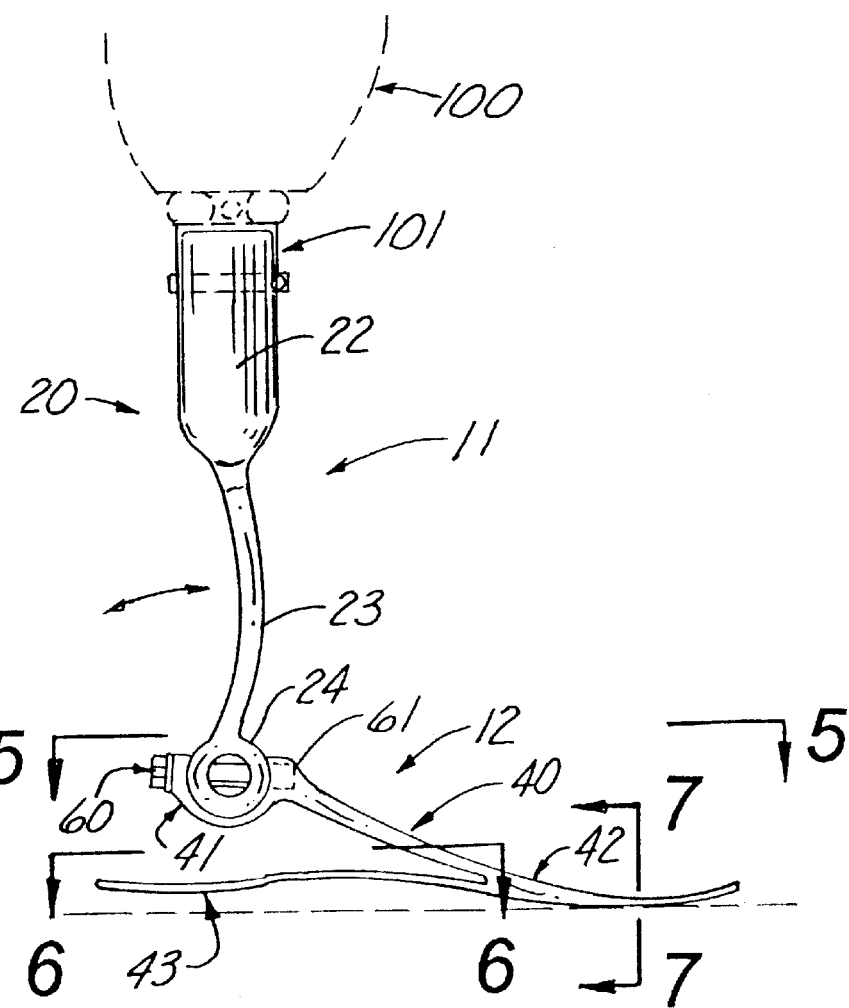
FIG. 2 is a side elevation view of the device in the more rigid support orientation.

In the orientation depicted in FIGS. 1 and 2, the convex curvature of the intermediate segment 23 of the leg pylon member 20 is faced towards the toe segment 42 of the foot member 40 to allow the user to run faster due to the increased stiffness produced by the reverse curvature between the leg pylon member 20 and the toe segment 42 of the foot member 40.

Figure 3:
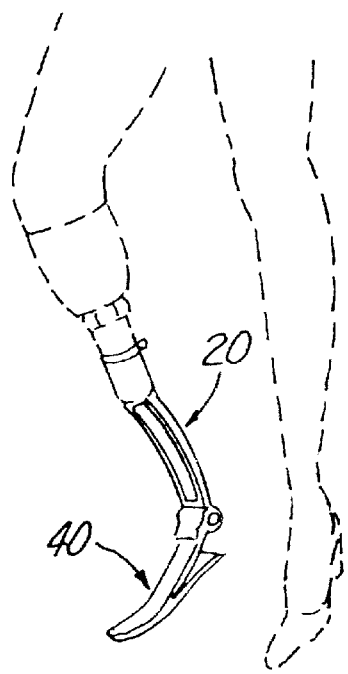
FIG. 3 is a perspective view of the angularly adjustable reversible prosthetic device oriented to provide more flexible support to the user's leg.

Furthermore, in the orientation depicted in FIGS. 3 and 4, the convex curvature of the intermediate segment 23 of the leg pylon member 20 is faced towards the heel segment 43 of the foot member 40 to provide greater flexibility to older individuals and moderate walkers due to the increased flexibility produced by the quasi-continuous curvature that exists between the concave surface of the leg pylon member 20 and the toe segment 42 of the foot member 40.

As can also be appreciated by reference to FIGS. 3 and 4, the angular adjustment feature allows the user to vary the angular orientation between the leg pylon member 20 and the foot member 40 to raise the heel segment 43 of the foot member 40 upwardly to accommodate footwear having different height heels. This feature is particularly helpful to female amputees who wish to wear high heels as a fashion statement.

Turning now to FIGS. 5 through 10, it can be seen that adjustable flexibility/rigidity has been designed into both the foot member 40 and the pylon leg members 20 of the device 10.

As shown in FIGS. 5 through 7, the flexibility/rigidity of the foot member 40 can be varied in both the toe 42 and heel 43 segments by first removing selected portions of those segments to create elongated voids 70 such as recesses or apertures. The amount of material removed will dictate the amount of increased flexibility that will be created in the affected segments 42 and/or 43.

Furthermore, this invention also contemplates the use of foot inserts 71 that can be slidably and/or releasably received within the voids 70 to selectively vary the flexibility/rigidity of the segments 42, 43 both by virtue of the number of inserts 71 employed and by the position of the individual inserts within the respective voids 70.

Turning now to FIGS. 8 through 10, it can be seen that the intermediate segment 23 of the leg pylon member 20 is provided with an enlarged central aperture 80 which is dimensioned to receive a plurality of removable vertically oriented rib elements 81. The flexibility/rigidity of the leg pylon member 20 is dictated by the number of rib elements 81 that are installed within the aperture 80 at any given time.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An angularly adjustable reversible prosthetic leg device for use with a prosthetic socket having a tube clamp adapter wherein the device comprises:

a leg unit including a leg pylon member having an upper segment adapted to be captively engaged by said tube clamp adapter, an intermediate segment, and a lower segment;

a foot unit including a foot member having an ankle segment, a toe segment, and a heel segment wherein, the foot member is further provided with a recess extending downwardly through the ankle segment and dimensioned to slidably engage the lower segment of the leg pylon member in a lateral fashion; and, means for captively securing the leg pylon member at a desired angular orientation about a horizontal axis relative to the foot member.

2. The device as in claim 1 wherein said upper segment has a generally cylindrical configuration dimensioned to be received in the tube clamp adapter.

3. The device as in claim 2 wherein said intermediate segment has a generally thin flat concavo-convex configuration.

4. The device as in claim 3 wherein the recess in the ankle segment is further dimensioned to receive the lower segment of the leg pylon member in a first position and in a second oppositely facing position.

5. The device as in claim 3 wherein the concavo-convex intermediate segment of the leg pylon member is provided with an enlarged aperture having a plurality of removable rib elements.

6. The device as in claim 1 wherein the upper, intermediate and lower segments are fabricated integrally with one another.

7. The device as in claim 6 wherein the ankle, toe, and heel segments are formed integrally with one another.

8. The device as in claim 1 wherein the ankle, toe, and heel segments are formed integrally with one another.

9. The device as in claim 1 wherein the lower segment of the leg pylon member has a generally cylindrical configuration and the ankle segment of the foot member has an arcuate recess dimensioned to pivotally receive the generally cylindrical configuration.

10. The device as in claim 9 wherein both the lower segment of the leg pylon member and said arcuate recess are provided with elongated ridged teeth that are at least temporarily engageable with one another.

11. The device as in claim 9 wherein the generally cylindrical lower segment of the leg pylon member is provided with a pair of elongated slots and the ankle segment of the foot member is provided with a pair of apertures that extend across said arcuate recess and are alignable with said pair of elongated slots.

12. The device as in claim 11 further comprising:

a pair of bolts dimensioned to be received through said pair of apertures in the ankle segment of the foot member and the pair of elongated slots in the lower segment of the leg pylon member.

13. The device as in claim 1 further comprising:

means for adjusting the flexibility/rigidity of the leg pylon member.

14. The device as in claim 13 further comprising:

means for adjusting the flexibility/rigidity of the foot member.

15. The device as in claim 1 wherein the intermediate segment of the leg pylon member is provided with a plurality of removably vertical rib elements for varying the flexibility/rigidity of the leg pylon member.

16. The device as in claim 1 further comprising:

means for adjusting the flexibility/rigidity of the foot member.

17. The device as in claim 16 wherein said means for adjusting the flexibility/rigidity of the foot member includes at least in part at least one elongated void formed in a selected portion of said foot member.

18. The device as in claim 17 wherein said means for adjusting the flexibility/rigidity of the foot member further includes at least one insert dimensioned to be removably received in said at least one void.

19. The device as in claim 18 wherein said at least one insert is adapted to be slidably received in said at least one void.

20. The device as in claim 1 wherein said selected portion of the foot member comprises the ankle segment.

* * * * *